United States Patent [19]

Friddell

[11] Patent Number: 4,974,247
[45] Date of Patent: Nov. 27, 1990

[54] SYSTEM FOR RADIOGRAPHICALLY INSPECTING AN OBJECT USING BACKSCATTERED RADIATION AND RELATED METHOD

[75] Inventor: Kenneth D. Friddell, Seattle, Wash.

[73] Assignee: The Boeing Company, Seattle, Wash.

[21] Appl. No.: 124,625

[22] Filed: Nov. 24, 1987

[51] Int. Cl.$^5$ .......................................... G01N 23/203
[52] U.S. Cl. ....................................... 378/90; 378/46;
378/86; 378/87
[58] Field of Search ....................... 378/44, 45, 48, 46,
378/47, 86, 87–89, 90

[56] References Cited

U.S. PATENT DOCUMENTS

| | | |
|---|---|---|
| 3,644,736 | 2/1972 | Kato et al. . |
| 3,704,370 | 11/1972 | Shelton . |
| 3,925,660 | 12/1975 | Albert . |
| 3,983,397 | 9/1976 | Albert . |
| 4,048,496 | 9/1977 | Albert . |
| 4,149,081 | 4/1979 | Seppi . |
| 4,260,885 | 4/1981 | Albert . |
| 4,292,419 | 9/1981 | Kamada et al. . |
| 4,366,252 | 12/1982 | Weaver . |
| 4,511,927 | 4/1985 | Bauer . |
| 4,519,092 | 5/1985 | Albert . |
| 4,538,290 | 8/1985 | Nakamura ............................ 378/86 |
| 4,544,949 | 10/1985 | Kurihara . |
| 4,599,740 | 7/1986 | Cable . |
| 4,611,340 | 9/1986 | Okazaki . |
| 4,698,832 | 10/1987 | Kuusi ................................... 378/90 |
| 4,750,196 | 6/1988 | Harding ............................... 378/86 |
| 4,799,247 | 1/1989 | Annis et al. ......................... 378/87 |

*Primary Examiner*—Carolyn E. Fields
*Assistant Examiner*—David P. Porta
*Attorney, Agent, or Firm*—Finnegan, Henderson, Farabow, Garrett & Dunner

[57] ABSTRACT

A system and related method are provided for radiographically inspecting an object, located in a radiation path at an inspecting location, using backscattered radiation to obtain a radiographic representation of the object. Radiation, from a source, is transmitted to the selected location. A portion of the transmitted radiation passes through the object and is backscattered by an illuminator to a radiation detecting device. Another portion of the transmitted radiation interacts with and is backscattered by the object to the detecting device. The detecting device generates response signals in response to both portions of the backscattered radiation. The response signals are used to obtain the radiographic representation of the object.

16 Claims, 4 Drawing Sheets (1) $R_1 = a \times \sqrt{\theta}$ (2) $R_1 = a \times \theta$ (3) $R_1 = a \times \theta^2$ (4) $R_2 = a \times \sqrt{\pi - \theta}$ (5) $R_2 = a \times (\pi - \theta)$ (6) $R_2 = a \times (\pi - \theta)^2$

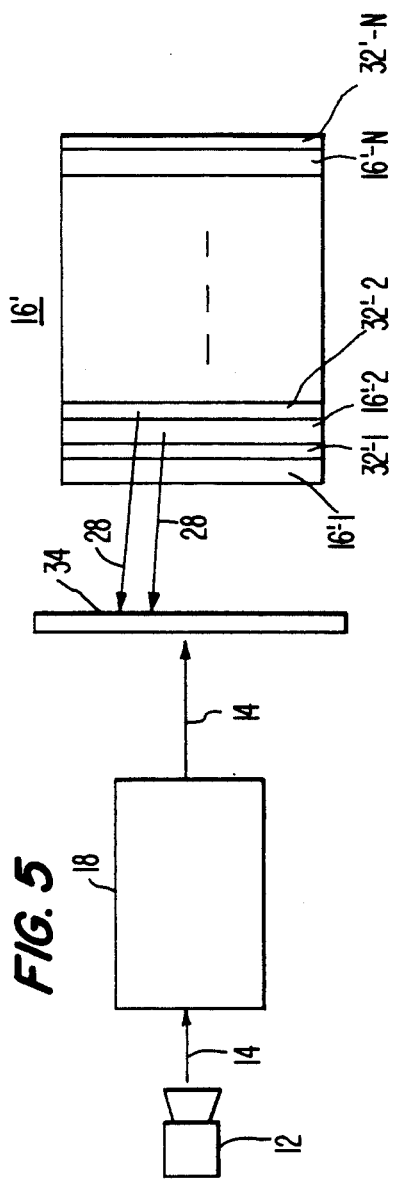
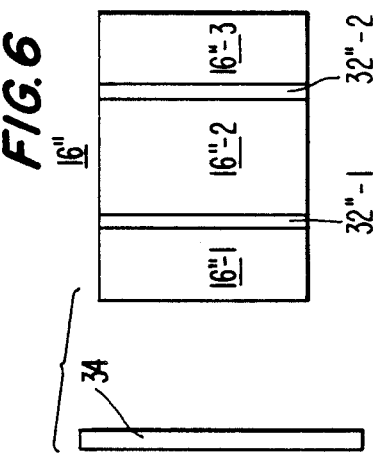

SYSTEM FOR RADIOGRAPHICALLY INSPECTING AN OBJECT USING BACKSCATTERED RADIATION AND RELATED METHOD

BACKGROUND OF THE INVENTION

I. Field of the Invention

This invention relates generally to a system and related method for inspecting an object, and more specifically, a system and related method for radiographically inspecting an object, positioned at a selected inspecting location, using backscattered radiation to generate a radiographic image of the object.

II. Background Information

Systems and techniques are known for radiographically inspecting an object using radiation directed to, and passing through, the object. Such systems typically use a radiation source to generate radiation and to direct the radiation along a radiation path toward a selected inspecting location at which the object is positioned. Detectors, disposed in the radiation path, beyond the selected inspecting location, are operative to detect the radiation passing through the object and to generate signals in response to the "through radiation." The through radiation, which has been attentuated by the object, and the signals generated in response to the attenuated, through radiation provide a representation of the object for use in generating a radiographic image.

Certain known radiographic inspection systems further include "backscatter detectors" disposed in the radiation path between the radiation source and the selected inspecting location. These "backscatter detectors" detect radiation interactive with and "backscattered" by an object at the selected location, and generate signals in response to the detected radiation. That is, the "backscatter detectors" detect, and generate response signals for, radiation traveling "backward" from an object as a result of compton scattering or photoelectric fluorescence. Such inspection systems, having detectors which detect both the radiation passing through and "backscattered" by an object at the inspecting location, provide an improved image of the object.

Although an improved image is obtained when through and backscattered radiation are detected utilizing both through radiation and backscatter detectors, the need often arises to exclude through radiation detectors from radiographic inspection systems. Notwithstanding the useful representational information provided by through radiation detectors, the limited amount of space available for the inspection system, or the particular nature or location of the object to be inspected, may make the placement of through radiation detectors beyond the inspecting location impossible or extremely difficult. This is often the case where the object to be inspected is an object like a wall, large box or container, or a large structure like an aircraft wing or fuselage.

Typically, in such instances, a representation of the object is obtained using only backscatter detectors and the radiation backscattered by the object. No account of the radiation passing through the object is taken. Accordingly, the quality of the image suffers as compared with the image obtained when both through radiation and backscatter detectors are used.

Conventional inspection systems which rely only on backscattered radiation to obtain a representation of the object do not include apparatus or methods for significantly improving the representation of the object beyond the quality of image obtained when only response signals generated from backscatter radiation are used.

SUMMARY OF THE INVENTION

Accordingly, the present invention has as an object to provide a radiographic inspection system which utilizes only backscatter detectors to obtain a representation of an object, but which utilizes both backward traveling compton scattered and photoelectric fluorescent radiation, and radiation passing through the object in obtaining the representation.

The present invention also has as an object to provide a radiographic inspection system capable of producing a high resolution image of the object being inspected.

Additional objects and advantages of the invention will be set forth in the description which follows, and in part will be obvious from the description or may be learned by practice of the invention. The objects and advantages of the invention may be realized and obtained by means of the instrumentalities and combinations particularly pointed out in the appended claims.

To achieve the foregoing objects, and in accordance with the purposes of the invention as embodied and broadly described herein, there is provided a system for radiographically inspecting an object disposed at a selected inspecting location along a radiation path. The system comprises a source of radiation for directing a beam of radiation in a first direction along the radiation path, and an illuminator, disposed in the radiation path of the generated radiation, beyond the selected inspecting location. The illuminator is activated in response to the reception of radiation passing through an object disposed at the selected location, and scatters (compton scattering and photoelectric fluorescence) the received radiation in a second direction along the radiation path, opposite the first direction, back through the object at the selected location. The system further comprises detection means, disposed in the radiation path between the selected inspecting location and the radiation source. The detection means is operative to receive first backscattered radiation traveling in the second direction from the illuminator, back through the object at the inspecting location, and is operative to receive second backscattered radiation interacting with the object at the inspecting location. The detection means generates signals responsive to the received first and second backscattered radiation.

A related method is also provided. The method comprises the steps of: transmitting a radiation beam along a radiation path in a first direction toward the selected inspecting location; backscattering radiation (compton scattering and photoelectric fluorescence) passing along the radiation path in the first direction and through an object at the inspecting location, in a second direction along the radiation path, opposite the first direction, back through the object at the selected location; detecting radiation traveling through the object at the inspecting location and backscattered in the second direction and detecting radiation interacting with the object and backscattered in the second direction; and generating signals in response to the backscattered radiation.

BRIEF DESCRIPTION OF THE DRAWINGS

FIG. 5 is a schematic diagram of an illuminator having a plurality of sections, incorporating the teachings of the subject invention; and FIG. 6 is a schematic diagram of an object having a plurality of sections with associated bond lines or surfaces therebetween for holding or bonding the associated sections.

DESCRIPTION OF THE PREFERRED EMBODIMENTS

Reference will now be made in detail to present preferred embodiments of the invention, examples of which are illustrated in the accompanying drawings.

Figure 1:
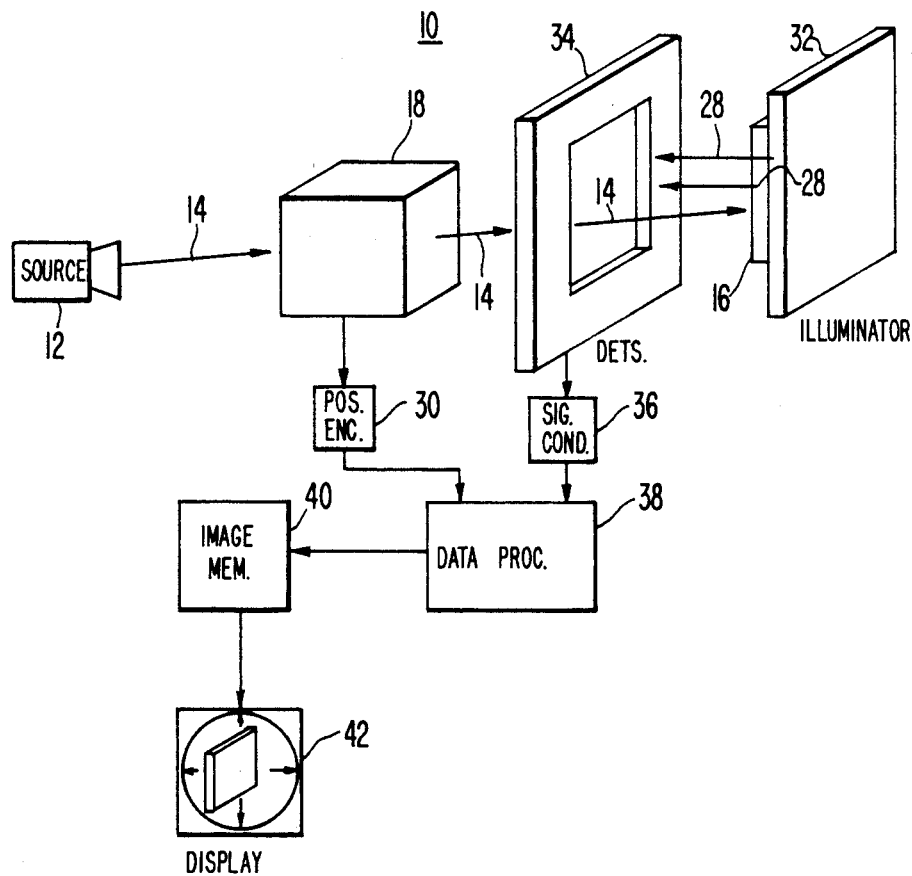
FIG. 1 is a schematic block diagram of a system for radiographically inspecting an object incorporating the teachings of the subject invention.

A preferred embodiment of the system for radiographically inspecting an object disposed at a selected inspecting location using backscattered radiation is shown in FIG. 1 and is generally represented by the numeral 10. The term "backscattered radiation," as here used, refers to "backward" traveling radiation produced both from compton backscattering and photoelectric fluorescence.

This system includes a radiation source 12 which is operative to transmit radiation along a radiation path in a first direction, indicated by line 14, toward a selected location. An object 16 is shown in position at the selected location. Radiation source 12 preferably transmits either X-ray or gamma radiation. Accordingly, source 12 may be, for example, a 320 KVP X-ray tube and housing available from Siefert X-Ray Corp. of Fairview Village, Pennsylvania.

Figure 2:
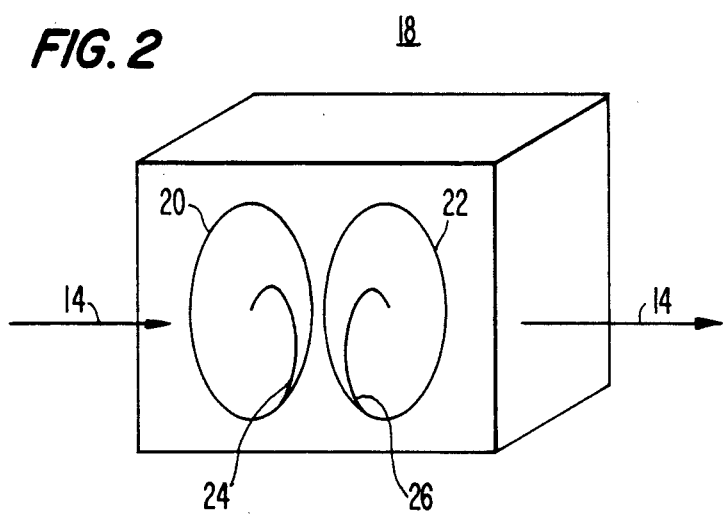
FIG. 2 is a block diagram of a scanning-area selecting means which is used in the radiographic inspection system of the present invention.

System 10 further includes a scanning area selecting means 18 interposed between radiation source 12 and the selected inspecting location. As here embodied, scanning area selecting means 18 is a selecting means of the type disclosed in a simultaneously-filed co-pending U.S. Pat. application, of the same Assignee disclosing a SYSTEM FOR RADIOGRAPHICALLY INSPECTING A RELATIVELY STATIONARY OBJECT AND RELATED METHOD. Accordingly, as shown in FIG. 2, scanning area selecting means 18 includes a first rotating disk 20 and a second rotating disk 22. Both rotating disks 20 and 22 are formed of a material having a high atomic number such as, for example, lead. First rotating disk is disposed in the radiation path between radiation source 12 and second rotating disk 22. Accordingly, the radiation beam from radiation source 12 is transmitted to first rotating disk 20, the radiation beam being incident upon first rotating disk 20. First rotating disk 20 includes a spirally-shaped aperture 24. As disk 20 is rotated, aperture 24 of disk 20 operates to sequentially select and transmit spirally-shaped area portions of the radiation beam along the radiation path in the first direction towards second rotating disk 22 and the selected inspecting location. The sequential selection and transmission of spirally-shaped portions of the radiation beam is performed inasmuch as rotating disk 20 blocks radiation from source 12, except for radiation incident at aperture 24 of disk 20. Rotation of disk 20 is described in detail hereinafter. The shape of aperture 24 of rotating disk 20 is also described in detail hereinafter.

Rotating disk 22 is also disposed in the radiation path. Rotating disk 22 is disposed between rotating disk 20 and the selected inspecting location, and is preferably aligned with rotating disk 20 such that each disk rotates about the same axis which is coincident with the center of each disk. Planes defining surfaces of the disks are substantially parallel. Rotating disk 22 includes a spirally-shaped aperture 26. As disk 22 is rotated, aperture 26 operates to sequentially select and transmit, from the spirally selected portions from disk 20, area portions of radiation each corresponding to a pencil beam of radiation. The pencil beam areas of radiation are transmitted along the radiation path to preselected area portions of the inspecting location. Rotating disk 22 operates to sequentially select and transmit pencil beam areas of radiation by blocking the spirally-shaped portions of radiation from rotating disks 22 except for the radiation incident at aperture 26.

Rotating disks 20 and 22 are rotated at separate speeds using for example, separate motors and rotating gears (not shown). The rotation of disk 20 is relatively slow in comparison with the rotation of rotating disk 22. Rotating disk 20 is kept stationary during a predetermined time while second rotating disk 22 is rotated through one complete revolution of 360°. The predetermined time period during which the second rotating disk 22 is rotated through a complete revolution may be, for example, 1/30th of a second, but may vary in accordance with the intensity of the radiation beam from source 12. This predetermined time period may preferably be increased as the intensity of the radiation beam from source 12 is decreased to provide a larger signal to noise ratio. At the end of the predetermined time, first rotating disk 20 is rotated to a new position.

Rotating disk 20 is rotated through a distance corresponding to the width of aperture 24 of disk 20. As disk 20 and 22 rotate, apertures 24 and 26 are themselves rotated, cooperatively, to permit a single pencil beam area of radiation to pass from radiation source 12 to area portions of the inspecting location in the manner described above. That is, as aperature 24 of rotating disk 20 is rotated to permit spirallyshaped portions of the radiation beam from source 12 to be sequentially transmitted to rotating disk 22, aperture 26 is rotated in a manner such that alignment exists at only a single point between each of apertures 24 and 26. The alignment which exists between these points of apertures 24 and 26, allowing selection of pencil beam areas of the inspecting location, is further described below.

Figure 3:
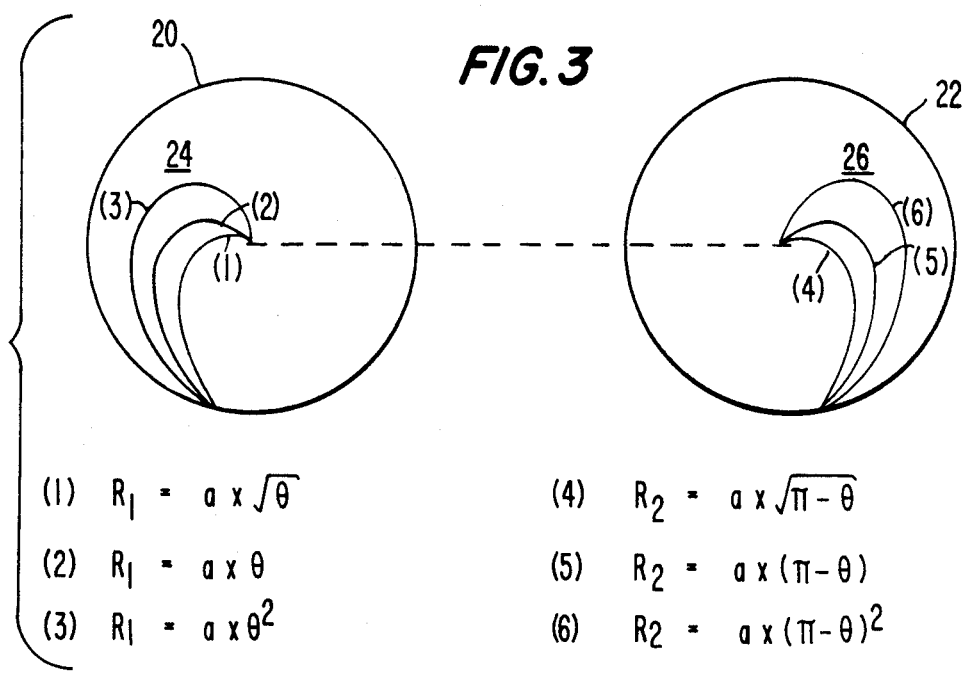
FIG. 3 is a schematic diagram of a pair of rotating disks, showing spiral slits therein, which are used in the radiographic inspection system of the present invention.

Preferably, the spirally-shaped apertures 24 and 26 of disks 20 and 22, respectively, are shaped in the form of spiral curves. The spiral curves may have a variety of specific shapes such as, for example, parabolic, linear (Archimedian), quadradic or logarithmic (equiangular) shapes. Referring to FIG. 3, specific exemplary shapes for corresponding spiral curves for rotating disks 20 and 22 are shown. Also shown are equations for the corresponding exemplary parabolic, Archimedian and quadradic spiral curves of rotating disks 20 and 22.

Equations in polar coordinates for curved aperture 24 of disk 20 are given below.

$$R_1 = a \times \sqrt{\theta} \text{ (parabolic spiral)} \tag{1}$$

$$R_1 = a \times \theta \text{ (spiral of Archimedes)} \tag{2}$$

$$R_1 = a \times \theta^2 \text{ (quadradic spiral)} \quad (3)$$

In the foregoing equations, a represents a constant, $\theta$ represents the polar angle in radian measure from a horizontal axis, and $R_1$ denotes the radius vector of disk 20. Corresponding equations for curved aperture 26 of disk 22 are given below.

$$R_2 = a \times \sqrt{(\pi - \theta)} \quad (4)$$

$$R_2 = a \times (\pi - \theta) \quad (5)$$

$$R_2 = a \times (\pi - \theta)^2 \quad (6)$$

In equations (4), (5) and (6) which respectively correspond to equations (1), (2) and (3), a represents a constant, $\theta$ represents the polar angle in radian measure from a horizontal axis, and $R_2$ denotes the radius vector of disk 22.

The width of both apertures 24 and 26 is preferably between 0.1 and 1.00 millimeters.

Figure 4C:
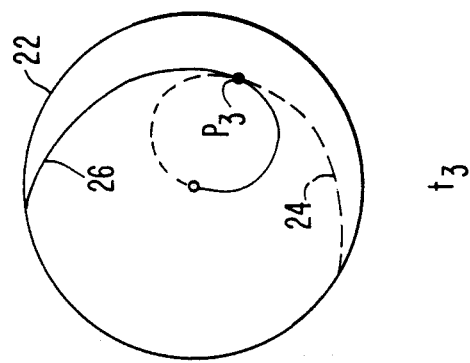
FIGS. 4A, 4B and 4C are cross-sectional diagrams of the rotating disks showing the relative position of respective spiral slits during rotation.
Figure 4B:
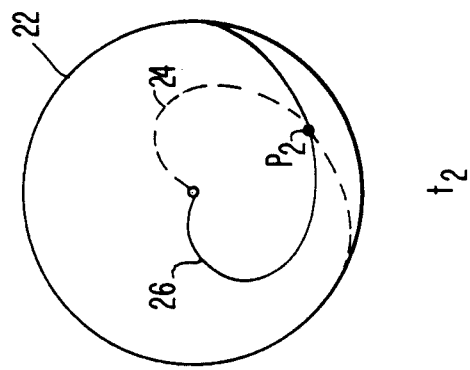
Figure 4A:
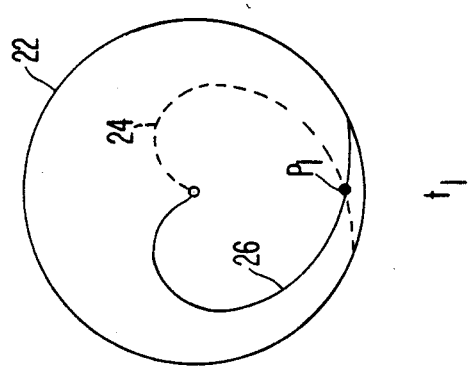

In FIGS. 4A, 4B and 4C, the manner in which apertures 24 and 26 are aligned to selectively transmit pencil beams of radiation is depicted. Curved apertures 24 and 26 are shown, superimposed cross-sectionally at times $t_1$, $t_2$ and $t_3$. The time spanning times $t_1$, $t_2$ and $t_3$ is less than a predetermined time period for rotating second disk 22 through a complete revolution. Accordingly, aperture 24 of disk 20 is shown in the same position during each of times $t_1$, $t_2$ and $t_3$. On the other hand, aperture 26 of disk 22 is shown in different positions corresponding to positions assumed by aperture 26 during rotation. At each time $t_1$, $t_2$ and $t_3$ points of cross-sectional alignment of aperture 24 and 26 exist at cross-sectional points $P_1$, $P_2$ and $P_3$, respectively. These points indicate the location of pencil beams of radiation from source 12 passing through both rotating disks. As aperture 26 rotates, aperture 26 sequentially selects and transmits pencil beams of radiation, from points as shown, to individual point-area portions of the inspecting location at which object 16 is located. With the rotation of disk 20, points of alignment for the disks are moved and pencil beams of radiation are sequentially selected and transmitted by disk 22 to the remaining portions of the detection area of detection means 32, the sequential selection and transmission resulting in a spiral sweep of point area-portions of the inspecting location.

System 10 further includes scanning-area determining means 30. As here embodied, the scanning-area determining means comprises a position encoder 30 for determining the area portions of the selected inspecting location selected by the scanning area selecting means. That is, position encoder 30 is responsive to scanning area selection means 18 to determine the point of alignment between disks 22 and 24 to obtain the location of the area portion of the first radiation beam transmitted from source 12 to the object 16 at the selected inspecting location at any given time. Position encoder 30 may comprise, for example, means for sensing edge markings on each of disks 20 and 22, and for utilizing information as to the mathematical relationship between the edge markings for each disk and the location of the spiral aperture for the disk relative to the markings. This exemplary position encoder would also comprise a photodetector for receiving light reflections from disk edge markings to determine the present rotational position of a disk.

A portion of the radiation transmitted to the selected inspecting location interacts with object 16 and is backscattered by the object in a second direction, indicated by line 28, opposite to the first direction. This is the only portion of radiation detected by conventional inspection system utilizing backscatter detectors. Another portion of the radiation transmitted to the inspecting location passes through and emerges from object 16 at the inspecting location.

The radiation passing through object 16, the "through radiation," is received by an "illuminator" of the inspection system. The illuminator 32, which is disposed in the radiation path, beyond the selected inspecting location, is "activated" in response to the reception of through radiation from object 16. Illuminator 32 of the system of the present invention backscatters the received radiation, also in the second direction, along the radiation path. Specifically, illuminator 32 scatters, absorbs and re-radiates the received radiation in the second direction back through object 16.

The received radiation interacts with illuminator 32 through one or more of the three interaction mechanisms, photoelectric, compton or pair production, depending on the incident energy spectrum and the atomic number of the illuminator material. The photoelectric interaction will cause the lower energy regions of the spectrum to be absorbed and then re-radiated as fluorescent radiation in all directions, including the backward direction. The compton interaction will cause the medium energy regions by the spectrum to scatter in all directions, including the backward direction.

The composition and physical characteristics of illuminator 32 are preferably selected to achieve an optimum intensity and energy level of backscatter for the radiation passing through an object at the inspecting location. Specifically, to achieve the desired intensity and energy level of backscatter, illuminator 32 is chosen in accordance with the object being inspected. For example, to enhance the through radiation backscattered when objects such as heavy metals are inspected for location and outlines, illuminator 32 preferably comprises a low atomic sheet material comprising, for example, carbons, hydrocarbons, or oxygen compounds. An illuminator 32 compromising the described sheet material is preferrably between 0.1 and 5 centimeters thick.

The specific intensity and energy level of radiation backscattered by the sheet materials is dependent upon the energy level of source 12. The backscattered radiation intensity and energy may be increased by increasing the energy level of the radiation generated by source 12, the source energy being increased in order to vary the image contrast for different types of objects, such as metals, having high atomic numbers.

As another example, to inspect complex multi-level boxes or inaccessible objects, illuminator means 32 may comprise a liquid such as a hydrocarbon or water-based fluid and a liquidretaining means, positioned adjacent the selected inspecting location and the object 16 to be inspected. As here embodied, the liquid retaining means comprises any thin membrane chamber in which the liquid may be retained. The chamber of the liquid-retaining means may actually be placed adjacent and beyond object 16, or may be part of the object itself, the object being designed to include the chamber to facilitate radiographic inspection. The thin membrane chamber may be emptied of the liquid when inspection of the object is not being performed.

Alternatively, for inspecting low atomic number materials such as hydrocarbon plastics, an illuminator 32 comprising a high atomic number solid material, having a thickness from 0.001 to 0.1 cm, may be utilized. Illuminator 32 may also comprise a liquid containing a high atomic number solid such as barium salt, or a high atomic number liquid such as liquid mercury, and a thin membrane chamber. As described above, the liquid may be retained in the membrane chamber. An illuminator 32 comprising a liquid with a high atomic number solid or comprising a high atomic number liquid is preferably used for inspecting a complex structure containing low atomic number material such as, for example, hydraulic hoses.

System 10 further includes a detection means 34 disposed in the radiation path between the selected inspecting location and radiation source 12. The detection means is operative to receive first backscattered (compton scattered and fluorescent radiation) radiation traveling in the second direction from illuminator 32 through object 16 at the inspecting location, and operative to receive second backscattered radiation interacting with object 16. The detection means generates signals responsive to the first and second backscattered radiation. As here embodied, the detection means preferably includes electronic radiation detectors 34 disposed between the selected inspecting location and radiation source 12, and operative to perform the above-described functions. Electronic radiation detectors 34 include, for example, plastic scintillator-photomultiplier combination electronic radiation detectors available from Bicron Corp. of Newbury, Ohio.

As shown in FIG. 1, the detection means further includes a signal conditioning means. As here embodied, the signal conditioning means comprises an analog to digital converter 36, responsive to electronic radiation detectors 34, for converting analog voltage/current response signals generated by electronic radiation detectors 34 to digital form. Analog to digital converter 36 may be, for example, a model 7612D analog to digital converter available from Tektronix, Inc. of Beaverton, Oregon, which converts received analog signal into digital signals.

A data processing means of the detection means is responsive to position encoder 30 and electronic detectors 34 (via analog to digital converter 36) for processing the signals generated by electronic radiation detectors 34. As here embodied, the processing means comprises a data processor 38 which establishes a correspondence between selected area portions of the inspecting area to which the radiation beam passes, and response signals generated as radiation is passed through the portions of object 16 located at the selected area portions of the inspecting location. Response signals for each area portion of the inspecting location are obtained and processed by data processor 38.

The detection means also includes an image memory 40 responsive to data processor 38 for storing the signals processed by processor 38, and a display means governed by data processor 38 for generating a radiographic image of the inspection area of object 16 in accordance with the signals stored by image memory 40. Image memory 40 may be, for example, a model ST-100 memory device available from Star Technologies, Inc. of Sterling, Virginia. The display means, here embodied as display means 42, may be for example a model NEC Multisync, monitor available from NEC Home Electronics, Inc. of Wood Dale, Illinois, provides a visual display of an image of object 16.

Since the electronic radiation detector receives first backscatter radiation passing through object 16, and backscattered (backward compton scattering and photoelectric fluorescence) from illuminator 32, and second backscatter radiation directly from object 16 (backward compton scattering and photoelectric fluorescence), the signals and image of object 16 stored and displayed are significantly different in information content as compared with signals and images provided by conventional inspection systems having only backscatter detectors.

Referring to FIG. 5, another preferred embodiment of the system of the present invention for radiographically inspecting an object having a plurality of substantially parallel sections is described. This preferred embodiment is essentially identical to the preferred embodiment described above, but includes an illuminator 32' having a plurality of sections 32'-1, 32'-2 and 32'-N each disposed immediately adjacent and beyond one of a plurality of sections of an object 16', 16'-1, 32'-2 and 2'-N, as shown in FIG. 5.

Each of the sections of illuminator 32' comprises a thin membrane chamber for retaining a liquid containing a high atomic number solid such as a barium salt, the illuminator sections also comprising the liquid when so retained.

At any given time, a single one of sections 32'-1 through 32'N of illuminator 32' is loaded with the liquid. Illuminator 32 is thereby utilized to backscatter radiation passing through a corresponding section or sections of object 16' located between source 12 and the liquid-filled section of illuminator 32', and to prevent radiation from source 12 from further penetrating object 16'. In this manner, an image of the corresponding section or sections is obtained.

The image obtained is only that of the corresponding section or sections located between source 12 and the liquid-filled illuminator section and does not include any representation of successive sections of object 16'.

To obtain an image of any one of section 16'-1–16'-N of obejct 16', an inspection of the sections of object 16', between source 12 and the desired section, but not including the desired section, is made. Response signals obtained in the inspection are stored. An inspection of the sections of object 16' between source 12, and the desired section, including that section, is also made, and corresponding response signals stored. As described above, to inspect sections of object 16' not including the desired section, the thin membrane chamber between source 12 and the desired section, and nearest the desired section is filled with liquid. To inspect the sections of object 16' including the desired section, the chamber of illuminator 32' immediately beyond the desired section is filled with the high atomic number liquid. Thereafter, data processor 38 is used to subtract the response signals for the inspections to obtain a representation of the desired section of object 16'. The resulting response signals of the desired section may thereafter be stored in memory 40 and visually displayed by display means 42.

Referring to FIG. 6, another preferred embodiment of the present invention is described. As shown in FIG. 6, sections 16''-1–16''-3 of object 16'' are bonded together with a bonding material at junctions 32''-1–32''-3. The bonding material at junction 32''-1 contains a portion of high atomic number material such as barium while the bonding material of junction 32''-2 contains a portion of a different higher atomic number material such as lead. With this embodiment, the radiation source 12 is operated at a high voltage, e.g., 50 Kvp, which produces a radiation spectrum that excites the barium, which has a fluorescence voltage of 33 kev, to undergo photoelectric fluorescence. The amount and spatial variation of fluorescent radiation from junction 32"-1 is directly proportional to the amount of barium in bonding material at junction 32"-1.

Increasing the operating voltage of radiation source 12 to a higher voltage such as, for example, 100 kvp and placing copper shields, having a thickness from 0.01 to 0.3 cm, between source 12 and means 18 will produce a radiation spectrum with little lower energy content at the barium fluorescent energy but a large content of radiation at the lead fluorescent energy. The amount and spatial variation of the radiation from junction 32"-2 is directly proportional to the amount of lead in the bonding material at junction 32"-2. Accordingly, based on the photoelectric fluorescence from each of the junctions detectable by detectors 34 at respective source voltages, the uniformity of the high atomic number material in a junction may be determined. Assuming that the high atomic material is uniformly distributed in the bonding material, the uniformity of the bonding material between sections 16"-1 and 16"-3 may also be determined. The integrity of the bond between sections may be evaluated according to the uniformity of the bonding material at a junction.

In view of the foregoing, it should be understood that in addition to disclosure of a system for radiographically inspecting an object, a related method for doing the same is also disclosed. As embodied herein, the method comprises the steps of transmitting a radiation beam along a radiation path in a first direction 14 toward the selected inspecting location at which an object 16/16' is positioned; backscattering radiation passing along the radiation path in the first direction 14 and through the object 16/16' at the inspecting location, in a second direction 28 along the radiation path, opposite the first direction, through the object 16/16' at the selected location; detecting radiation traveling through the object 16/16' at the inspecting location and backscattered in the second direction 28 and detecting radiation interacting with the object 16/16' and backscattered in the second direction 28; and generating signals such as with detectors 34 in response to the backscattered radiation for use in generating an image of the object.

It should be apparent to those skilled in the art that various modifications may be made to the system for radiographically inspecting an object using backscattered radiation to obtain a radiographic representation of the object without departing from the scope or spirit of the invention. Thus, it is intended that the invention cover modifications and variations of the invention, provided they come within the scope of the appended claims and their legally entitled equivalents.

I claim:

1. A system for radiographically inspecting an object disposed at a selected inspecting location along a radiation path, comprising:

a source of radiation for directing a beam of radiation in a first direction along the radiation path;

scanning area selecting means, interposed in the radiation path between the radiation source and the selected inspecting location, for sequentially selecting area portions of the beam of radiation and for transmitting the selected area portions to preselected area portions of the inspecting location;

scanning-area determining means, responsive to said scanning area selecting means, for determining the area portions of the inspecting location selected by the scanning-area selecting means;

an illuminator, disposed in the radiation path of the generated radiation, beyond the selected inspecting location, activated in response to the reception of radiation passing through the object disposed at the selected location, for backscattering the received radiation and providing a source of fluorescence in a second direction along the radiation path, opposite the first direction, through the object at the selected location, detection means, disposed in the radiation path between the selected inspecting location and the radiation source, operative to receive first backscattered and fluorescent radiation traveling in the second direction from the illuminator through the object at the inspecting location, and operative to receive second backscattered and fluorescent radiation interacting with the object at the inspecting location, the detection means generating signals responsive to the received first and second backscattered and fluorescent radiation, and including a data processing means responsive to the scanning-area determining means for processing the response signals corresponding to the first and second backscattered and fluorescent radiation to obtain a radiographic representation of the object.

2. The system according to claim 1, wherein the detection means further includes display means, responsive to the data processing means, for generating an image of the object according to the radiographic representation of the object.

3. The system according to claim 1, wherein the detection means further includes a signal conditioning means, responsive to the detecting means for conditioning the response signals, and wherein the data processing means is responsive to the signal conditioning means for processing the signals generated by the signal conditioning means.

4. The system according to claim 2, wherein the detection means further comprises an image memory, responsive to the data processing means for storing the signals processed by the data processing means, said display means being responsive to the signals stored by the image memory to generate the radiographic image of the object.

5. The system according to claim 1, wherein said illuminating means comprises a solid material having a low atomic number.

6. The system according to claim 1, wherein the illuminator comprises a solid material having a high atomic number.

7. A system for radiographically inspecting an object disposed at a selected inspecting location along a radiation path, comprising:

a source of radiation for directing a beam of radiation in a first direction along the radiation path;

scanning area selecting means, interposed in the radiation path between the radiation source and the selected inspecting location, for sequentially selecting area portions of the beam of radiation and for transmitting the selected area portions to preselected area portions of the inspecting location;

scanning-area determining means, responsive to said scanning area selecting means, for determining the area portions of the inspecting location selected by the scanning-area selecting means;

an illuminator, disposed in the radiation path of the generated radiation, beyond the selected inspecting location, activated in response to the reception of radiation passing through the object disposed at the selected location, for backscattering the received radiation and providing a source of fluorescence in a second direction along the radiation path, opposite the first direction, through the object at the selected location, said illuminator comprising liquid-retaining means positioned adjacent the selected inspecting location and the object, and a liquid having a low atomic number, disposed within the liquid retaining means; and detection means, disposed in the radiation path between the selected inspecting location and the radiation source, operative to receive first backscattered and fluorescent radiation traveling in the second direction from the illuminator through the object at the inspecting location, and operative to receive second backscattered and fluorescent radiation interacting with the object at the inspecting location, the detection means generating signals responsive to the received first and second backscattered and fluorescent radiation, and including a data processing means responsive to the scanning-area determining means for processing the response signals corresponding to the first and second backscattered and fluorescent radiation to obtain a radiographic representation of the object.

8. A system for radiographically inspecting an object disposed at a selected inspecting location along a radiation path, comprising:

a source or radiation for directing a beam of radiation in a first direction along the radiation path;

scanning area selecting means, interposed in the radiation path between the radiation source and the selected inspecting location, for sequentially selecting area portions of the beam of radiation and for transmitting the selected area portions to preselected area portions of the inspecting location;

scanning-area determining means, responsive to said scanning area selecting means, for determining the area portions of the inspecting location selected by the scanning-area selecting means;

an illuminator, disposed in the radiation path of the generated radiation, beyond the selected inspecting location, activated in response to the reception of radiation passing through the object disposed at the selected location, for backscattering the received radiation and providing a source of fluorescence in a second direction along the radiation path, opposite the first direction, through the object at the selected location, said illuminator comprising liquid-retaining means positioned adjacent the selected inspecting location and the object, and a liquid having a high atomic number, disposed within the liquid retaining means; and detection means, disposed in the radiation path between the selected inspecting location and the radiation source, operative to receive first backscattered and fluorescent radiation traveling in the second direction from the illuminator through the object at the inspecting location, and operative to receive second backscattered and fluorescent radiation interacting with the object at the inspecting location, the detection means generating signals responsive to the received first and second backscattered and fluorescent radiation, and including a data processing means responsive to the scanning-area determining means for processing the response signals corresponding to the first and second backscattered and fluorescent radiation to obtain a radiographic representation of the object.

9. A system for radiographically inspecting an object having a plurality of sections disposed at a selected inspecting location along a radiation path, comprising:

a source of radiation for directing a beam of radiation in a first direction along the radiation path;

scanning area selecting means, interposed in the radiation path between the radiation source and the selected inspecting location, for sequentially selecting area portions of the beam of radiation and for transmitting the selected area portions to preselected area portions of the inspecting location;

scanning-area determining means, responsive to said scanning area selecting means, for determining the area portions of the inspecting location selected by the scanning-area selecting means;

an illuminator comprising a plurality of sections each having liquid retaining means, each of said liquid-retaining means being positioned immediately beyond a successive one of the plurality of sections of the object at the selected inspecting location, and a liquid, disposed within one of the liquid retaining means, said illuminator being activated in response to the reception of radiation passing through the object disposed at the selected location, for backscattering the received radiation and providing a source of fluorescence in a second direction along the radiation path, opposite the first direction, through the object at the selected location; and detection means, disposed in the radiation path between the selected inspecting location and the radiation source, operative to receive first backscattered and fluorescent radiation traveling in the second direction from the illuminator through the object at the inspecting location, and operative to receive second backscattered and fluorescent radiation interacting with the object at the inspecting location, the detection means generating signals responsive to the received first and second backscattered and fluorescent radiation, and including a data processing means responsive to the scanning-area determining means for processing the response signals corresponding to the first and second backscattered and fluorescent radiation to obtain a radiographic representation of the sections of the object located between the radiation source and the illuminator.

10. The system according to claim 9, wherein the data processing means includes means for subtracting a first representation obtained for sections of the object disposed between the radiation source and a desired section of the object, not including the desired section, and a next representation obtained for sections of the object disposed between the radiation and the desired section, including the desired section, to obtain a representation of the desired section of the object.

11. A system for radiographically inspecting an object having a plurality of sections disposed at a selected inspecting location along a radiation path, comprising:

a source of radiation for directing a beam of radiation in a first direction along the radiation path;

scanning area selecting means, interposed in the radiation path between the radiation source and the selected inspecting location, for sequentially selecting area portions of the beam of radiation and for transmitting the selected area portions to preselected area portions of the inspecting location;

scanning-area determining means, responsive to said scanning area selecting means, for determining the area portions of the inspecting location selected by the scanning-area selecting means;

an illuminator having a plurality of sections each comprising a a high atomic number element uniformly interspersed in a bonding material, each of the plurality of sections of the illuminator being distributed at a junction between successive sections of the object at the selected inspecting location, said illuminator being activated in response to the reception of radiation passing through the object disposed at the selected location, for backscattering the received radiation and providing a source of fluorescence in a second direction along the radiation path, opposite the first direction, through the object at the selected location; and detection means, disposed in the radiation path between the selected inspecting location and the relative source, operative to receive first backscattered and fluorescent radiation traveling in the second direction from the illuminator through the object at the inspecting location, and operative to receive second backscattered and fluorescent radiation interacting with the object at the inspecting location, the detection means generating signals responsive to the received first and second backscattered and fluorescent radiation, and including a data processing means responsive to the scanning-area determining means for processing the response signals corresponding to the first and second backscattered and fluorescent radiation to obtain a radiographic representation of the distribution of the bonding material between the successive section of the object.

12. The system according to claim 11, wherein each of the plurality of sections of the illuminator comprises a unique high atomic number element, and wherein intensity and energy levels for the radiation from the radiation source is varied to determine the distribution of the bonding material between certain successive sections of the object in accordance with the atomic number of the unique high atomic number element of the section of the illuminator having the bonding material and distributed between the certain successive sections.

13. A method for radiographically inspecting an object disposed at a selected inspecting location along a radiation path, comprising the steps of:

transmitting a radiation beam along a radiation path in a first direction toward the selected inspecting location;

sequentially selecting area portions of the beam of radiation and transmitting the selected area portions to preselected area portions of the inspecting location;

determining the area portions of the inspecting location to which the sequentially selected area portions of the beam of radiation are being transmitted;

backscattering radiation passing along the radiation path in the first direction and through an object at the inspecting location, in a second direction along the radiation path, opposite the first direction, through the object at the selected location;

detecting radiation traveling through an object at the inspecting location and backscattered in the second direction and detecting radiation interacting with the object and backscattered in the second direction;

generating signals in response to the detected radiation; and processing the response signals for the sequentially selected area portions of the inspecting location to obtain a radiographic representation of the object at the inspecting location.

14. The method according to claim 13, wherein the step of processing includes the substep of generating an image of the object according to the radiographic representation of the object.

15. The method according to claim 13, wherein the step of processing includes the substep of storing the response signals to generate an image of the object.

16. A method for radiographically inspecting an object disposed at a selected inspecting location along a radiation path, the object including a plurality of sucessive sections with bonding material distributed between the successive sections for bonding the successive sections of the object, the method comprising the steps of:

transmitting a radiation beam along a radiation path in a first direction toward the selected inspecting location;

sequentially selecting area portions of the beam of radiation and transmitting the selected area portions to preselected area portions of the inspecting location;

determining the area portions of the inspecting location to which the sequentially selected area portions of the beam of radiation are being transmitted;

backscattering radiation passing along the radiation path in the first direction and through an object at the inspecting location, in a second direction along the radiation path, opposite the first direction, through the object at the selected inspecting location;

detecting first radiation traveling through an object at the inspecting location and backscattered in the second direction and detecting second radiation interacting with the object and backscattered in the second direction;

generating signals in response to the detected first and second radiation; and processing the response signals for the sequentially selected area portions of the inspecting location to obtain a radiographic representation of the distribution of the bonding material between the successive sections of the object.

* * * * *

UNITED STATES PATENT AND TRADEMARK OFFICE
CERTIFICATE OF CORRECTION

PATENT NO. : 4,974,247

DATED : November 27, 1990

INVENTOR(S) : Kenneth D. FRIDDELL

It is certified that error appears in the above-identified patent and that said Letters Patent is hereby corrected as shown below:

Claim 1, column 10, line 15, "location," is changed to --location; and--.

Claim 11, column 13, lines 27-28, "relative" is changed to --radiation--.

Signed and Sealed this

Twelfth Day of May, 1992

Attest:

DOUGLAS B. COMER

*Attesting Officer*   Acting Commissioner of Patents and Trademarks